United States Patent [19]

Warner, Jr. et al.

[11] 4,282,206

[45] Aug. 4, 1981

[54] METHOD OF PROTECTING HUMAN SKIN FROM ULTRAVIOLET RADIATION

[75] Inventors: Paul L. Warner, Jr., Clarence; F. Christopher Zusi, Williamsville, both of N.Y.

[73] Assignee: Westwood Pharmaceuticals Inc., Buffalo, N.Y.

[21] Appl. No.: 94,419

[22] Filed: Nov. 15, 1979

[51] Int. Cl.³ .............................................. A61K 7/42
[52] U.S. Cl. .................................... 424/59; 544/165
[58] Field of Search ........................... 544/165; 424/59

[56] References Cited

U.S. PATENT DOCUMENTS 3,453,313  7/1969  Margot et al. .................. 544/165
3,772,275  11/1973  Hernestam et al. ............. 544/165

OTHER PUBLICATIONS

Pifferi et al., *Chem. Abstracts*, vol. 57, (1962), pp. 631–632.

*Primary Examiner*—Henry R. Jiles
*Assistant Examiner*—R. W. Ramsuer
*Attorney, Agent, or Firm*—Morton S. Simon

[57] ABSTRACT

Reaction of 4-nitrophenacyl bromide with morpholine affords the novel intermediate 1-(4-nitrophenyl)-2-morpholinylethanone which when reduced yields the novel sunscreen 1-(4-aminophenyl)-2-morpholinylethanone.

2 Claims, 1 Drawing Figure

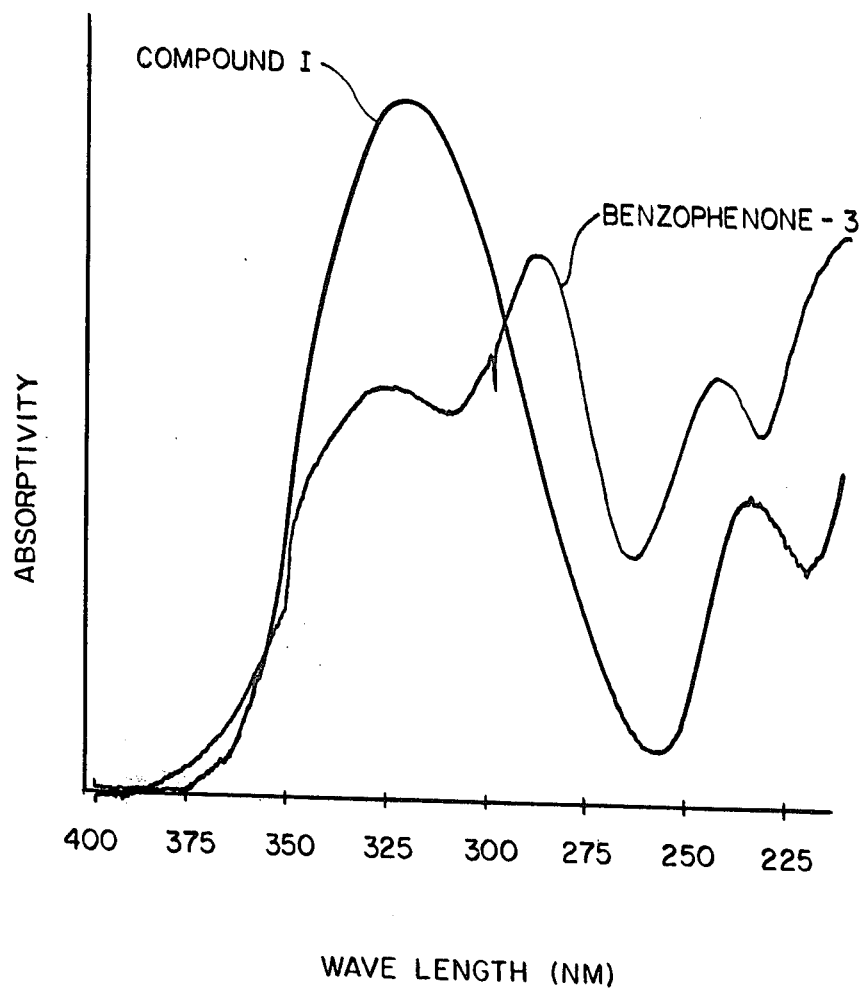

METHOD OF PROTECTING HUMAN SKIN FROM ULTRAVIOLET RADIATION

I. DESCRIPTION

This invention relates to compositions for use in filtering ultraviolet radiation to screen out rays that are harmful to mammalian (human or animal) skin or organic materials, thereby protecting against the burning and degrading effects of such radiation.

It is known that electromagnetic radiation emanating from the sun or from a source of ultraviolet light can have a detrimental and deleterious effect on paints, plastics, and other substances. It is also known that such radiation is harmful and damaging to human skin since radiation in this range of wavelength causes cutaneous sunburn and has been identified as carcinogenic. It is also acknowledged that certain radiation can directly or indirectly cause an adverse effect or response to the skin and various organs, particularly in connection with the influence of other agents, such as coal tar extracts and various plant extracts. More particularly, the influence of sunlight or ultraviolet radiation in connection with the use of drugs can result in adverse effects such as edema, hyperpigmentation, vesicle formation, and exaggerated sunburn. Other skin disorders such as polymorphic light eruptions and erythematosis are significantly exaggerated by exposure to light in this wavelength range.

Electromagnetic radiation within the ultraviolet and visible spectrum incident upon an object can be blocked by a mechanical barrier, for example, by a film of titanium dioxide, or the like, which prevents passage of all radiation regardless of wavelength. Another method which permits the greater part of the incident radiation to pass through and which takes out only a specified spectral range depends upon the employment of a selective sunscreen agent. A sunscreen agent is a substance which interacts photochemically with radiation of a given wavelength and removes all or part of the radiation. Thus, important criteria for evaluation of sunscreen agents are: (1) the ability to absorb light, i.e., to display an ultraviolet or visible light-absorption spectrum and (2) to absorb the light efficiently, that is to have a molar absorptivity or extinction coefficient which is sufficiently high to provide effective sunscreening at relatively low concentrations. In general, an extinction coefficient or molar absorptivity of at least 20,000 is desirable.

In connection with the human skin, pigmentation or tanning is generally produced by radiation of the ultraviolet range roughly from about 2,900 to about 4,000 A. Radiation in the wavelength range of about 2,950 A. to 3,150 A. is sufficiently potent to produce severe erythema within a few hours. This range is often referred to as the burning range. At wavelengths above the burning range, e.g., from about 3,300 to 3,900, the radiation produces direct tanning after exposure of sufficient duration and intensity. Hence, it is desirable to screen out the burning rays of the sun without significant reduction in the tanning rays.

Other effects of ultraviolet radiation are of significant importance with respect to commercial products and the photochemical decomposition thereof. Many materials are either unstable when subject to such radiation or are effected to the extent that they become undesirable. Plastic materials, paints, and pigments when exposed to radiation undergo substantial decomposition resulting in the development of undesirable colors, odors, loss of transparency, and the like. Accordingly, prolonged exposure of such materials to ultraviolet radiation is a matter of significant importance. It is also an object of the invention to provide methods for the protection of light-sensitive subjects from the photodecomposition and deleterious effects caused by exposure to significant quantities of ultraviolet radiation. A further object of the invention is to provide compositions which can be applied topically to human skin and which are useful as sunscreens and tanning agents. Another object of the invention is to provide compounds and compositions which can be admixed with or incorporated into or applied to the surface of light-sensitive materials for the purpose of screening or filtering ultraviolet radiation. Another object of the invention is to provide cosmetically acceptable formulations of sunscreen agents which are substantially non-staining when exposed to sunlight.

The sunscreen of this invention has been found to be effective in preventing sunburn while facilitating tanning.

These and other objects of the invention are achieved by providing and using as a sunscreen agent a compound having the formula:

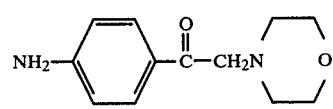

I

The compound of the present invention (I) is prepared by reacting 4-nitrophenacyl bromide with morpholine to produce the intermediate 1-(4-nitrophenyl)-2-morpholinylethanone (II) which is reduced to produce 1-(4-aminophenyl)- 2-morpholinylethanone (I).

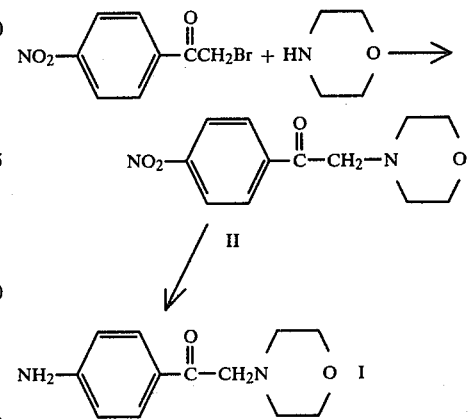

The process for producing the compound of the present invention (I) is more fully illustrated by Examples 1 and 2 which follow:

EXAMPLE 1

Preparation of 1-(4-nitrophenyl)-2-morpholinylethanone (II)

To an absolute ethanol (380 ml) suspension of p-nitrophenacyl bromide, 46.1 g. (0.19 mole), there were added, at 0°–5° C., over a period of 0.75 hour, 49.4 g. (0.19 mole) of morpholine. After addition was complete, the reaction mixture was stirred at 0°–5° C. for 0.5 hour. The reaction mixture was then filtered cold and the cake dissolved in chloroform (400 ml). Following extraction of the organic layer several times with water, the chloroform layer was dried over magnesium sulfate, and then filtered. Complete evaporation of the chloroform filtrate provided a solid which upon crystallization from alcohol gave 33.7 g. of the Compound II, m.p. 129°–130° C. (dec.).

EXAMPLE 2

Preparation of 1-(4-aminophenyl)-2-morpholinylethanone (I)

A suspension of 17.6 (0.07 mole) of Compound II and 1.76 g. of 10% palladium on carbon in 175 ml of ethanol was reduced using a Parr Hydrogenator until hydrogen uptake ceased. The catalyst was removed by filtration and the ethanol solution evaporated. The solid thus obtained was recrystallized twice from water and once from toluene whereby 5.1 g. of yellow needles of the Compound I were obtained, m.p. 107°–110° C., U.V.-$\lambda_{max}$ (Am): 318(21,000), 232(6,800).

As stated heretofore the compound of the present invention has valuable sunscreen activity. To demonstrate such activity its Protection Factor (PF) against U.V.B. light was evaluated in guinea pigs. Benzophenone-3 was employed as a comparative control. The procedure employed and the results of such study are more fully elaborated in the following Example 3.

EXAMPLE 3

The Protection Factor of Compound I against U.V.B. light was evaluated in the guinea pig. Benzophenone-3, an effective and recognized sunscreen agent, was used as a comparative control Six (6) healthy, Hartley strain guinea pigs, weighing approximately 300–400 grams and obtained from Elm Hill Breeding Labs were used for this study. The animals were conditioned for at least one week in a temperature controlled room with HEPA air filtration and 12-hour cycled lighting. The animals were housed in stainless steel cages and had access to Wayne Guinea Pig Diet and tested tap water ad libitum. The animals were identified by a color-coded marking system.

A 4% solution of Compound I in absolute alcohol, and a 4% solution of Benzophenone-3 in 50% alcohol were employed in the study.

Twenty-four (24) hours prior to use, the guinea pigs were clipped with an Oster ® clipper and depilated with NEET ® lotion. For the applications, the guinea pigs were placed on a restrainer. The backs of the guinea pigs were then divided into eight 1 cm$^2$ areas with Zonas ® tape. On each animal, 3 sites were left unprotected and irradiated for different periods (2, 3, and 4 minutes) in order to determine an MED for each individual animal. Three (3) other sites were covered with 0.05 ml of the 4% solution of Compound I in absolute alcohol (2 $\mu$l/cm$^2$) and 10 minutes later irradiated for 6, 12, and 18 minutes. The remaining 2 sites were covered with 0.05 ml of the 4% solution of Benzophenone-3 in 50% alcohol and 10 minutes later irradiated for 6 and 18 minutes.

The UVB light was produced by 6 Westinghouse FS40 bulbs. Following the irradiation, the backs of the guinea pigs were rinsed with tepid tap water and patted dry.

Six (6) hours later, the sites were graded for erythema on a scale of 0–4 (Draize, et al., J Pharm Exp Ther 82: 377, 1944).

The individual erythema scores and the calculated protection factor for the 4% solution of Compound I in absolute alcohol and for the 4% solution of Benzophenone-3 in 50% alcohol are reported in Table 1 below.

TABLE 1

Individual Erythemal Values, MED Determinations (circled), and Calculated Protection Factor (PF)

| | Time Minutes | Guinea Pig No. 1 | 2 | 3 | 4 | 5 | 6 | Mean PF |
|---|---|---|---|---|---|---|---|---|
| Control Sites | 2 | 0 | 0 | 1 | 1 | 0 | 0 | |
| | 2.3+ | | | | | | 1+ | |
| | 3 | 1 | 0+ | 1 | 2 | 1 | 3 | |
| | 3.5+ | | 1+ | | | | | |
| | 4 | 1 | 2 | 2 | 1 | 1 | 2 | |
| (4% sol. of Comp. I) | 6 | 1 | 1 | 1 | 0 | 0 | 1 | |
| | 12 | 1 | 2 | 1 | 1 | 1 | 1 | |
| | 18 | 4 | 2 | 2 | 3 | 2 | 3 | |
| PF++ | | 2.0 | 1.7 | 3.0 | 3.0 | 4.0 | 2.6 | 2.72 |
| (4% sol. of Benzo-phenone-3) | 6 | 1 | 1 | 1 | 0 | 1 | 1 | |
| | 18 | 3 | 2 | 1 | 2 | 1 | 3 | |
| PF++ | — | 2.0 | 1.7 | 3.0 | 6.0 | 2.0 | 2.6 | 2.88 |

+Estimated.
++Based on individual control MED for each animal.

The results of Table 1 indicate that a 4% solution of the Compound I of the present invention had a protection factor of 2.7 against UVB light while a 4% solution of Benzophenone-3 had a protection factor of 2.9 against UVB light.

Thus under the conditions of the test, a 4% solution of the Compound I of the present invention had approximately the same protective effect as a 4% solution of Benzophenone-3 against UVB light in the guinea pig.

EXAMPLE 4

Ultraviolet spectra for the compound of the present invention (I) and for Benzophenone-3 were obtained on a Beckman DB-G spectrophotometer. In each case a 5.46 mg/l solution in ethanol was employed. The accompanying drawing represents a plot of the spectra obtained.

UVA agents are generally defined in the art as those compounds which absorb significant UV radiation in the range of about 320 to 400 nm.

UVB agents are generally defined in the art as those compounds which absorb significant UV radiation in the range of about 290 to 320 nm.

The drawing clearly demonstrates that the compound of the present invention (I) surprisingly and unexpectedly couples UVA and UVB absorption.

Benzophenone-3 is a prior art recognized UVA and UVB sunscreen.

It is evident from the drawing that the ethanolic solution of the compound (I) absorbs much stronger in the UVB range than does the ethanolic solution of Benzophenone-3 at the same concentration.

The drawing also shows that the compound (I) is a stronger UVA absorber than Benzophenone-3 from about 320 to 360 nm and is essentially comparable to Benzophenone-3 from about 360 to about 400 nm.

In general, the formulation itself does not affect the actual radiation-absorbing ability of the sunscreen agent but merely facilitates application and use thereof, e.g., by maintenance of an effective film of the sunscreen screen on the surface to be protected. As indicated above, the compound I of this invention is particularly useful as a sunscreen agent in pharmaceutical or cosmetic compositions. Accordingly, the invention includes pharmaceutical and cosmetic compositions which contain the sunscreen agent in a minor amount. Such compositions comprise, as a major portion thereof, a pharmaceutically or cosmetically acceptable carrier and the sunscreen agent in an amount effectively screening the burning rays of the sun. Generally, the sunscreen agent is employed in the pharmaceutical composition in an amount of from about 1% to about 10% by weight based on the total weight of the composition. In accordance with this invention, any suitable carrier or vehicle conventionally employed for suntan lotions or cosmetic creams, and the like, can be utilized. The particular vehicle or carrier employed is not an essential feature of the present invention and merely facilitates application to the skin.

The compound I of the present invention is readily formulated into and conventionally administered as, for example, cream, lotion or gel form.

The following formulae (Nos. 1–9) are offered in illustration of suitable oil-in-water lotions (Nos. 1–3), oil-in-water creams (Nos. 4–6) and hydroalcoholic gels (Nos. 7–9), incorporating the compound I of the invention.

It should be noted that in each of Formulae Nos. 1–9 the ingredients are in parts by weight.

| Lotion Formulae Nos. 1–3 | | | |
|---|---|---|---|
| | No. 1 | No. 2 | No. 3 |
| Compound I | 2.50 | 5.00 | 10.00 |
| Purified Water | 76.50 | 74.00 | 69.00 |
| Propylene Glycol, USP | 12.00 | 12.00 | 12.00 |
| Petrolatium, USP (Fonoline) | 5.84 | 5.84 | 5.84 |
| Stearyl Alcohol, USP | 2.00 | 2.00 | 2.00 |
| Amphoteric-6, CTFA | 0.66 | 0.66 | 0.66 |
| Carbomer 940, CTFA | 0.20 | 0.20 | 0.20 |
| Sodium Lauryl Sulfate, USP | 0.10 | 0.10 | 0.10 |
| Sorbic Acid, NF | 0.10 | 0.10 | 0.10 |
| Dried Sodium Phosphate | 0.10 | 0.10 | 0.10 |

Formulae Nos. 1–3 were prepared according to the following general procedure:

The propylene glycol and about 97% of the purified water are added to a stainless steel jacketed main mixing vessel of suitable size. The solution is heated to about 50°–55° C. and moderate mixing is initiated (using a Lightnin model NAR-100 air mixer with propeller type agitator or similar apparatus). The carbomer 940 is added and mixing is continued until all of the carbomer is in solution. The stearyl alcohol and petrolatum are added to a stainless steel premix vessel of suitable size and heated to and maintained at a temperature of about 62°–68° C. whereby an oil phase is produced. The remainder of the purified water is added to a small vessel of suitable size and heated to about 40°–45° C. Then the dried sodium phosphate is added thereto under rapid mixing. The mixing is continued until all the solid sodium phosphate is in solution. The aqueous solution of sodium phosphate is then added to the solution of carbomer 940, propylene glycol and purified water and mixed slowly until a homogeneous mixture is obtained. Then while continuing the slow mixing the sodium lauryl sulfate, amphoteric-6 and the sorbic acid are added. Mixing is continued until the mixture is homogenous. The temperature is then adjusted to about 60°–68° C. whereby an aqueous phase is produced. While mixing rapidly, the oil phase is added to the aqueous phase. The mixing is continued for about 10–15 minutes to form an emulsion. Then cold water is run into the jacket and the emulsion is cooled, under constant mixing, to a temperature of about 25°–30° C. whereby a lotion base is produced. The Compound I is added to a container of suitable size and a portion of the lotion base equal to about 3 to 5 times the weight of Compound I is added thereto. The lotion base and Compound I are mixed well to form a uniform suspension. The resultant mixture is passed one time through a stainless steel roller mill (preferably an Asra model 2 at a setting of 1–2). The resultant milled concentrate is collected in a suitable container then added to the remainder of the lotion base and mixed therewith at moderate speed for about one hour.

| Cream Formulae Nos. 4–6 | | | |
|---|---|---|---|
| | No. 4 | No. 5 | No. 6 |
| Compound I | 2.50 | 5.00 | 10.00 |
| Purified Water | 60.17 | 57.67 | 52.67 |
| Mineral Oil | 9.00 | 9.00 | 9.00 |
| Glyceryl Stearate/PEG-100 Stearate, CTFA | 5.00 | 5.00 | 5.00 |
| PEG-40 Stearate, CTFA | 5.00 | 5.00 | 5.00 |
| Isopropyl Palmitate | 5.00 | 5.00 | 5.00 |
| Propylene Glycol, USP | 5.00 | 5.00 | 5.00 |
| Squalane, CTFA | 3.00 | 3.00 | 3.00 |
| Sorbitol | 3.00 | 3.00 | 3.00 |
| Lanolin Alcohol | 1.00 | 1.00 | 1.00 |
| Cetyl Alcohol | 0.50 | 0.50 | 0.50 |
| Methylparaben | 0.25 | 0.25 | 0.25 |
| Propylparaben | 0.20 | 0.20 | 0.20 |
| Carbomer 934, CTFA | 0.18 | 0.18 | 0.18 |
| Triethanolamine | 0.18 | 0.18 | 0.18 |
| Quaternium-15, CTFA | 0.02 | 0.02 | 0.02 |

Formulae Nos. 4–6 were prepared according to the following general procedure:

99% of the purified water is added to a stainless steel jacketed main mixing tank (preferably a Groen model DN/TA 60SP, equipped with anchor blade and air mixer). High speed mixing is initiated (preferably through use of a Lightnin model NAR-100 air mixer equipped with propeller type agitator, or similar apparatus). Then the propylene glycol, methylparaben, sorbitol and carbomer 934 are slowly added. The mixing is continued for about 1 hour or until all ingredients are completely solubilized whereby an aqueous phase is produced. The isopropyl palmitate, squalane, mineral oil, propylparaben, lanolin alcohol, cetyl alcohol, PEG-40 stearate and glyceryl stearate/PEG-100 stearate are added to a jacketed stainless steel tank equipped with an airmixer (preferably a Groen model DN/TA 60SP, equipped with anchor blade and air mixer) and mixing and heating is initiated. The mixture is heated until all solids are melted. The temperature is then adjusted to and maintained at about 60°–65° C. whereby an oil phase is produced. The quaternium-15 and the remainder of the purified water are added to a small container of suitable size and mixed slowly therein using an air mixer equipped with propeller agitator (preferably a Lightnin model ARL or similar apparatus) until a clear solution is formed. When the oil phase and the aqueous phase are at the proper temperature, the oil phase is slowly added to the aqueous phase under moderate speed mixing (preferably employing a Lightnin Model NAR-100 air mixer). Mixing is continued for about 15–20 minutes until a homogeneous emulsion is obtained. The air mixer is then removed, cold water is introduced into the jacket and mixing is initiated with a side-scraping anchor type mixer (preferrably the Groen type or similar apparatus) at moderate speed (preferrably Groen speed setting 3-4). When the temperature reaches about 45° C. the aqueous solution of the quaternium-15 is added to the emulsion and mixing is continued until the emulsion is homogeneous whereby a cream base is produced. The Compound I is added to a container of suitable size and a portion of the cream base equal to about 3 to 5 times the weight of the Compound I is added thereto. The cream base and the Compound I are mixed well (by suitable means) to form a uniform suspension which is then passed one time through a stainless steel roller mill (preferrably an Asra model 2 at a setting of 1-2). The resultant milled concentrate is collected in a suitable container then added to the remainder of the cream base and mixed therewith at moderate speed for about one hour.

| Gel Formulae Nos. 7-9 | | | |
|---|---|---|---|
| | No. 7 | No. 8 | No. 9 |
| Compound I | 2.50 | 5.00 | 10.00 |
| SD Alcohol #40 | 55.00 | 55.00 | 55.00 |
| Animal Protein Derivative, CTFA | 3.00 | 3.00 | 3.00 |
| Purified Water | 38.30 | 35.80 | 30.80 |
| Hydroxyethylcellulose | 1.20 | 1.20 | 1.20 |

Formulae Nos. 7-9 were prepared according to the following general procedure:

The SD alcohol #40 and the Compound I are added to a stainless steel vessel of suitable size and mixed at moderate speed (preferrably using a Lightnin model NAR-100 air mixer equipped with propeller type blade, or similar apparatus) until all solids are in solution. The animal protein derivative is then added and mixing is continued until a homogeneous solution is obtained whereby an alcohol phase is produced. The purified water is added to a stainless steel main mix tank of suitable size and high speed mixing is initiated (preferrably using a Lightnin model NAR-100 air mixer equipped with propeller type blade, or similar apparatus). Then the hydroxyethylcellulose is slowly added. Mixing is continued until a gel is formed. The alcohol phase is then added to the gel in the main mixing tank and mixing is continued until the resultant gel is smooth and uniform (approximately 1 to 2 hours).

The compositions are applied to the skin in a known and conventional manner normally just prior to exposure to the sun.

The optimum proportion or concentration of the sunscreen agent in the composition will depend, at least in part, on the nature of the coating or film which is formed and left on the skin since some types of formulation will permit the formation of a screen of greater concentration of screening agent per unit area than others depending, for example, on viscosity and spreading power of the formulation and the permanence thereof in terms of resistance to wash off by perspiration or bathing.

The sunscreening compositions of this invention are not confined to any particular classes of cosmetics or to any particular formulations. Nevertheless, it is preferred to employ the compound of this invention along with a substantially greater amount of a dermatologically acceptable vehicle compatible with the skin, such as is exemplified in Formulae 1-9, above.

We claim:

1. A method for protecting human skin from ultraviolet radiation comprising applying to the skin to be protected an effective ultraviolet radiation-absorbing amount of 1-(4-aminophenyl)-2-morpholinylethanone in a vehicle suitable for topical administration.

2. The method, according to claim 1, wherein the 1-(4-aminophenyl)-2-morpholinylethanone is present in said vehicle in a concentration of from about 1% to about 10% by weight.

* * * * *